US00PP16949P3

(12) United States Plant Patent
Danziger

(10) Patent No.: US PP16,949 P3
(45) Date of Patent: Aug. 8, 2006

(54) ***TORENIA* PLANT NAMED 'DANCATBLUE'**

(50) Latin Name: ***Torenia* sp.**
Varietal Denomination: Dancatblue

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 9 days.

(21) Appl. No.: 10/929,419

(22) Filed: Aug. 31, 2004

(65) Prior Publication Data

US 2006/0048250 P1 Mar. 2, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—Foley & Lardner LLP

(57) ABSTRACT

A new and distinct *Torenia* plant named 'Dancatblue' particularly characterized by the combined features of pale violet-blue petals with violet-blue blotches on the side petals surrounding the corolla, and the lower petal with a centered yellow-green blotch near the base; bush, cascading, vigorous growth habit which maintains a compact, rounded growth habit; densely branched plant, gracefully cascading from hanging baskets; early flowering and year round blooming in moderate climate; suitable as an annual for hanging pots outdoors under partial shade; and good weather tolerance.

2 Drawing Sheets

Latin name of the genus and species of the plant claimed: *Torenia* sp.
Variety denomination: 'Dancatblue'.

BACKGROUND OF THE INVENTION

The present invention relates to a new and distinct cultivar of *Torenia* plant, botanically known as *Torenia* sp. of the Scrophulariaceae family, and hereinafter referred to by the cultivar name 'Dancatblue'.

The new cultivar originated from a cross made in a controlled breeding program in Moshav Mishmar Hashiva, Israel. The female parent is the *Torenia* sp. cultivar 'Blue Moon' (unpatented). The male parent is an unnamed, unpatented *Torenia* sp. bush type. 'Dancatblue' was discovered and selected by the inventor, Gabriel Danziger, as a flowering plant within the progeny of the stated cross in a controlled environment in Moshav Mishmar Hashiva, Israel.

Asexual reproduction of the new cultivar by soft tip cuttings was first performed in May, 2002 in Moshav Mishmar Hashiva, Israel and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'Dancatblue' which in combination distinguish this *Torenia* as a new and distinct cultivar:

1. Pale violet-blue petals with violet-blue blotches on the side petals surrounding the corolla, and the lower petal with a centered yellow-green blotch near the base;
2. Bush, cascading, vigorous growth habit which maintains a compact, rounded growth habit;

3. Densely branched plant, gracefully cascading from hanging baskets;
4. Early flowering and year round blooming in moderate climate;
5. Suitable as an annual for hanging pots outdoors under partial shade; and
6. Good weather tolerance.

Of the many commercial cultivars known to the inventor, the most similar in comparison to 'Dancatblue' is the parental cultivar *Torenia* sp. 'Blue Moon' (unpatented).

TABLE 1

| Characteristic | New Cultivar *Torenia* sp. 'Dancatblue' | Parental and Comparison Cultivar *Torenia* sp. 'Blue Moon' (unpatented) |
|---|---|---|
| Flower color | Pale Violet Blue | Violet Blue |
| Petal size (cm) | 1.5 cm width; 2.5 cm length | 3.5 cm width; 3.5 cm length |
| Growth habit | Bush cascading | Cascading |
| Flowering time | 8 weeks from planting | 10 weeks from planting |

'Dancatblue' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Moshav Mishmar Hashiva, Israel under conditions which closely approximate those generally used in commercial practice.

BRIEF DESCRIPTION OF THE DRAWINGS

The accompanying photographic drawings show typical flower and foliage characteristics of 'Dancatblue' with colors being as true as possible with illustrations of this type.

The first photograph shows a full flowering plant of 'Dancatblue' in its entirety in a hanging basket.

The second photograph shows a close-up of 'Dancatblue' flowers showing the pale violet-blue flowers with violet-blue blotches surrounding the corolla, and the central lobe blotched yellow at the base.

DETAILED BOTANICAL DESCRIPTION

The following observations, measurements and values describe the new cultivar as grown in Moshav Mishmar Hashiva, Israel, under conditions, which closely approximate those generally used in commercial practice. For use as a potted plant, optimal growth conditions include being grown outdoors in a moderate climate and indoors during the winter season. Irrigation and fertilization is recommended on a regular basis. 'Dancatblue' is best grown in full sunlight, but partial shade is required in mid summer. A fully grown 'Dancatblue' plant takes 3 months from planting a cutting in the summer season. 'Dancatblue' blooms year-round in moderate climate.

Color references are made to The Royal Horticultural Society Colour Chart (R.H.S.), except where general colors of ordinary significance are used. Color values were taken under daylight conditions at approximately noon in Moshav Mishmar Hashiva, Israel.

The age of the 'Dancatblue' plants described is 8 weeks. The 'Dancatblue' plants described were grown indoors in 16 cm pots in a glass greenhouse in Moshav Mishmar Hashiva, Israel, with the day temperatures ranging from 18° C. to 35° C. and night temperatures ranging from 16° C. to 25° C. Plants of 'Dancatblue' were fertilized up to a level of 59 ppm N, 35.4 ppm P and 94.4 ppm K.

Propagation: Tissue culture and soft tip cuttings.

Plant:

*Form.*—Bush cascading.

*Growth habit.*—Compact, rounded.

*Height.*—About 10 cm.

*Spread.*—60–80 cm.

*Blooming period.*—Year round in moderate climate.

*Cold tolerance.*—Frost tender; plants may be damaged by temperatures below 5° C.

*Vigor.*—Fully grown plant in 3 months during summer season.

Stem:

*Color.*—Green, RHS 143-A.

*Length.*—30 cm.

*Diameter.*—About 2 mm.

*Pubescence.*—Minimal.

*Branching.*—Between 5 and 10 main branches grow from the base and split into hundreds of secondary branches.

*Length of internodes.*—3–4 cm.

Foliage:

*Overall shape.*—Triangular-cordate.

*Base.*—Reniform.

*Tip.*—Acuminate.

*Margin.*—Serrate.

*Color.*—Center color of leaf: Green, RHS 137-A. Upper side: Green, RHS 137-A. Under side: Yellow-Green, RHS 146-B.

*Size of leaf.*—Width: About 3.5 cm. Length: About 4.5 cm.

*Leaf texture.*—Smooth, few hairs on every leaf, less than 0.3 mm long.

*Petioles.*—Length: 0.5 cm to 1 cm. Diameter: 1.5 mm. Color: Yellow-Green, RHS 146-B.

*Venation pattern.*—Anastomotic.

*Venation color.*—Yellow-Green, RHS 146-B (both upper and lower surfaces).

Flowers:

*Blooming period.*—All year round in moderate climate or greenhouse environment. In Israel, flowering is continuous from February until November in an outdoor garden.

*Flowering response.*—Less than 2 weeks after planting.

*Flowering stem.*—Flowers appear along the growing lateral stems.

*Number of flowers per lateral stem.*—About 4 to 6.

*Number of flowers per plant.*—About 200 to 400.

*Post production longevity.*—Up to 10 months.

*Lastingness of an individual bloom* (*vase life*).—Up to 2 to 4 days.

*Fragrance.*—None.

*Orientation at opening.*—Slanted upward.

*Type.*—Single.

*Shape.*—Corolla tube cylindrical or often broadened above, 2-lipped, the upper lip faintly 2-lobed, the lower lip 3-lobed.

*Flower width.*—About 2.8 cm.

*Flower depth.*—About 3 cm.

*Petals.*—Number: Four, fused. Length: Upper: About 2.5 cm. Sides: About 1.3 cm. Lower: About 1.5 cm. Width: Upper: About 1.5 cm. Sides: About 1 cm. Lower: About 1.3 cm. Shape: Upper: Overall: orbicular, Apex: truncate, Base: fused. Sides: Overall: spatulate, Apex: truncate, Base: fused. Lower: Overall: spatulate, Apex: truncate, Base: fused. Margin: Entire and undulated and picotee. Color: Pale violet-blue petals with violet-blue blotches on side petals surrounding the corolla, and yellow-green blotch in middle of lower petal near base. Mature: Upper Side: Upper petal: violet-blue shades, RHS 97-C and RHS 94-B at apex; side petals: violet-blue blotch, RHS 96-A; lower petal: yellow-green blotch, RHS 154-A in middle near base. Under Side: Upper and lower petals: pale violet-blue, RHS 97-C; side petals: pale violet-blue blotch, RHS 97-A. Margin: Upper petal: violet-blue, RHS 94-B (same for upper and under side of upper petal); lower petal: violet-blue, RHS 96-A (same for upper and under side of lower petal). Throat: Pale violet-blue, RHS 97-C; in the center of the flower, and yellow-green, RHS 154-A, in middle of lower petal. Immature: Upper Side: Upper petal: violet-blue shades, RHS 97-C and RHS 96-C near apex; side petals: violet-blue blotch, RHS 96-A; lower petal: yellow-green blotch, RHS 154-A in middle near base. Under Side: Upper and lower petals: pale violet-blue, RHS 97-C; side petals: pale violet-blue blotch, RHS 97-A. Margin: Upper petal, upper side: violet-blue, RHS 94-B and upper petal, under side: violet blue, RHS 94-C; lower petal, upper side: violet-blue, RHS 96-A and lower petal, under side: violet blue, RHS 95-B. Throat: Pale violet-blue, RHS 97-C, in the center of flower, and yellow-green, RHS 154-A, in middle of lower petal.

*Floral tube.*—Length: About 2.5 cm. Width: About 0.3 cm to 1.4 cm. Color: Outside: Pale violet-blue, RHS 97-A, and yellow, RHS 11-A. Inside: Pale violet-blue, RHS 97-A, and yellow, RHS 12-A.

*Sepals:* Number: 5. Length: About 1.8 cm. Width: About 0.8 cm. Shape: Two-lobed, 5 winged. Apex:

Acute. Base: Wedge-shaped. Margin: Undulated. Color: Yellow-green, RHS 144A.

*Peduncle.*—Diameter: About 1.2 cm. Length: About 0.5 cm to 1.4 cm. Color: Green, RHS 143-B.

*Bud.*—Shape: Oblong, cylindrical, ellipsoid, 5 winged. Size: Length: About 25 mm. Diameter: About 10 mm. Color: Apex: violet-blue, RHS 96A; Base: green, RHS 143-B.

Reproductive organs:

*Androecium.*—Stamen: 2 pairs per flower, fused; color: violet-blue, RHS 92-D. Anther: Length: about 0.4 cm (upper anther shorter — about 0.3 cm); Width: about 0.1 cm; color: violet-blue, RHS 92-B. Filament: Length: about 1.3 cm (lower filaments shorter — about 1.4 cm); Width: about 0.5 cm; color: violet-blue, RHS 92-D. Pollen: Amount produced: sparse; color: white, RHS N155-B.

*Gynoecium.*—Pistil: One per flower; about 2.3 cm in length. Stigma: Length: about 0.2 cm; width: about 0.2 cm, color: violet-blue, RHS 92-D. Style: Length: about 2 cm; color: violet-blue, RHS 92-D. Ovaries: 1; color: green, RHS 143-B.

Seed/fruit: None.

Pest/disease resistance and/or susceptibility: A standard preventative spray program is sufficient as no susceptibility was observed.

I claim:

1. A new and distinct *Torenia* plant named 'Dancatblue', as illustrated and described herein.

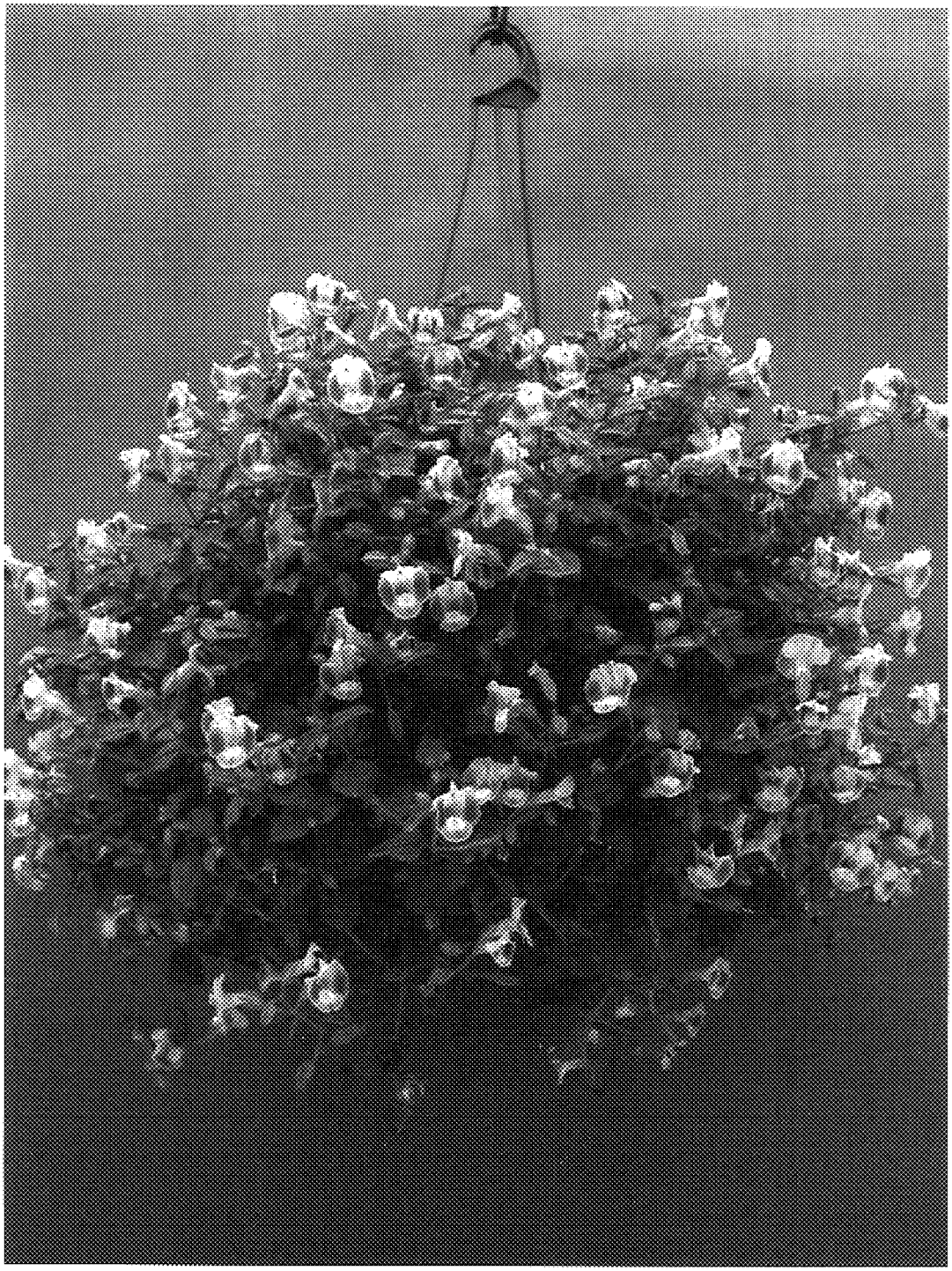

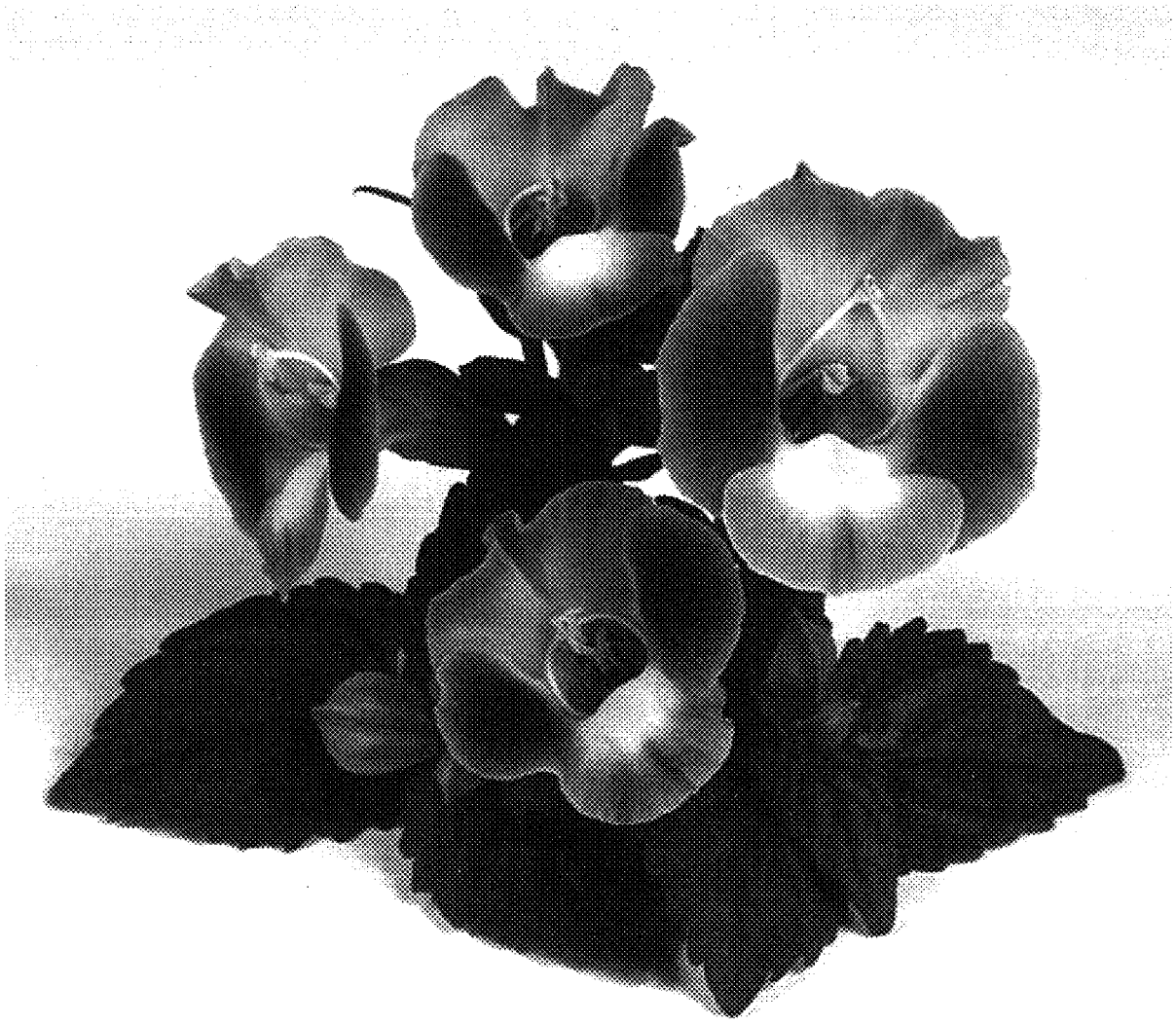

* * * * *